United States Patent
Pivetti et al.

(10) Patent No.: US 8,673,978 B2
(45) Date of Patent: Mar. 18, 2014

(54) POLYMORPHS AND SALTS

(75) Inventors: Fausto Pivetti, Parma (IT); Maurizio Delcanale, Parma (IT); Stefano Luca Giaffreda, Parma (IT); Marco Curzi, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 74 days.

(21) Appl. No.: 13/078,039

(22) Filed: Apr. 1, 2011

(65) Prior Publication Data

US 2011/0245346 A1  Oct. 6, 2011

(30) Foreign Application Priority Data

Apr. 1, 2010 (EP) ..................... 10158954

(51) Int. Cl.
*A61K 31/192* (2006.01)
*A61P 25/28* (2006.01)
*C07C 61/40* (2006.01)

(52) U.S. Cl.
USPC .......................................... 514/570; 562/492

(58) Field of Classification Search
USPC .......................................... 514/570; 562/492
See application file for complete search history.

(56) References Cited

U.S. PATENT DOCUMENTS

| 2007/0078114 A1 | 4/2007 | Hobden et al. |
| 2009/0312426 A1 | 12/2009 | Folleas et al. |
| 2010/0099768 A1 | 4/2010 | Raveglia et al. |
| 2011/0039934 A1 | 2/2011 | Pivetti et al. |

FOREIGN PATENT DOCUMENTS

| WO | 2004/074232 | 9/2004 |
| WO | 2008/036733 | 3/2008 |

OTHER PUBLICATIONS

U.S. Appl. No. 13/723,662, filed Dec. 21, 2012, Imbimbo.
U.S. Appl. No. 13/091,195, filed Apr. 21, 2011, Imbimbo, et al.
European Search Report in Application No. 09006930.3, issued Nov. 4, 2009.
Peretto I et al., J. Med. Chem, (2005) vol. 48, No. 18, Jan. 1, 2005, pp. 5705-5720.

*Primary Examiner* — San-Ming Hui
*Assistant Examiner* — Kathrien Cruz
(74) *Attorney, Agent, or Firm* — Oblon, Spivak, McClelland, Maier & Neustadt, L.L.P.

(57) ABSTRACT

Novel polymorphic forms and salts of 1-(3',4'-dichloro-2-fluorobiphenyl-4-yl)cyclopropanecarboxylic acid are useful for the prevention or treatment of Alzheimer's Disease.

17 Claims, 4 Drawing Sheets

POLYMORPHS AND SALTS

CROSS REFERENCES TO RELATED APPLICATIONS

This claims priority to European Patent Application No. 10158954.7, filed on Apr. 1, 2010, which is incorporated herein by reference in its entirety.

BACKGROUND OF THE INVENTION

1. Field of the Invention

The present invention relates to new crystalline forms and salts of 1-(3',4'-dichloro-2-fluorobiphenyl-4-yl)cyclopropanecarboxylic acid of the following formula:

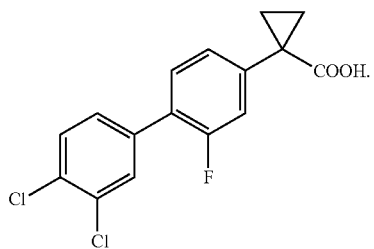

(Formula I)

The present invention also relates to methods for the prevention and treatment of medical conditions such as Alzheimer's Disease and other forms of dementia by administering such a crystalline form or salt.

2. Discussion of the Background

Alzheimer's Disease is a devastating neurological disorder affecting more than 37 million people worldwide. As yet, there are no approved drugs capable of preventing or reversing the disease. A particular focus of research and development efforts is on preventing formation of synaptotoxic β-amyloid (Aβ) peptide in the brain and its aggregation into plaques.

The gamma secretase modulator compound 1-(3',4'-dichloro-2-fluorobiphenyl-4-yl)cyclopropanecarboxylic acid was first described in patent application WO 2004/074232 as one of a large number of candidate therapeutic agents for neurodegenerative diseases such as Alzheimer's disease. That application does not disclose any crystal forms or specific salts of the compound.

Polymorphism is defined as the ability of a substance to crystallize in more than one crystal lattice arrangement. Polymorphism can influence many aspects of solid state properties of a drug. Different crystal modifications of a substance may differ considerably from one another in many respects, such as their solubility, dissolution rate and bioavailability.

SUMMARY OF THE INVENTION

Accordingly, it is one object of the present invention to provide novel polymorphs of 1-(3',4'-dichloro-2-fluorobiphenyl-4-yl)cyclopropanecarboxylic acid.

It is another object of the present invention to provide novel salt forms of 1-(3',4'-dichloro-2-fluorobiphenyl-4-yl)cyclopropanecarboxylic acid.

These and other objects, which will become apparent during the following detailed description, have been achieved by the inventors' discovery that that 1-(3',4'-dichloro-2-fluorobiphenyl-4-yl)cyclopropanecarboxylic acid can exist in multiple crystalline polymorphic forms. Furthermore, it has been possible to prepare a selection of novel salts of the compound. These new polymorphs and salt forms are particularly useful in the preparation and further development of effective therapies for Alzheimer's disease.

Thus, the present invention provides a first novel polymorphic form of 1-(3',4'-dichloro-2-fluorobiphenyl-4-yl)cyclopropanecarboxylic acid, termed Form I.

The present invention further provides a second polymorphic form of 1-(3',4'-dichloro-2-fluorobiphenyl-4-yl)cyclopropanecarboxylic acid, termed Form II.

In a further aspect the present invention provides a third polymorphic form of 1-(3',4'-dichloro-2-fluorobiphenyl-4-yl)cyclopropanecarboxylic acid, termed Form III.

In another aspect the present invention provides salts of 1-(3',4'-dichloro-2-fluorobiphenyl-4-yl)cyclopropanecarboxylic acid selected from the group consisting of: Na, K, Ca, L-Arginine, D-Arginine, and L-Lysine salts.

In a further aspect, the present invention provides a pharmaceutical composition comprising any of the novel polymorphic or salt forms of 1-(3',4'-dichloro-2-fluorobiphenyl-4-yl)cyclopropanecarboxylic acid of the invention, and a pharmaceutically acceptable carrier.

In yet another aspect, the present invention provides a method for preventing or treating a neurodegenerative disease in a patient, comprising administering an effective amount of a polymorphic form of 1-(3',4'-dichloro-2-fluorobiphenyl-4-yl)cyclopropanecarboxylic acid, or a salt of 1-(3',4'-dichloro-2-fluorobiphenyl-4-yl)cyclopropanecarboxylic acid selected from the group consisting of: Na, K, Ca, L-Arginine, D-Arginine, and L-Lysine salts.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

It has now been found that 1-(3',4'-dichloro-2-fluorobiphenyl-4-yl)cyclopropanecarboxylic acid can exist in multiple crystalline polymorphic forms, three of which are stable and have been identified and are characterized in the Examples. The term "crystalline polymorph" refers to a crystal modification that can be characterized by analytical methods such as X-ray powder diffraction (XRPD) and Infra-Red (IR)-spectroscopy, or by its melting point (for instance, as measured by Differential Scanning Calorimetry, DSC).

In a first aspect the invention relates to crystalline polymorph Form I of the compound of Formula I:

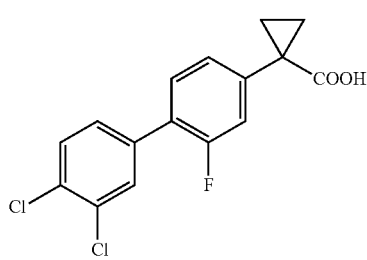 [SMILES: O=C(O)C1(c2ccc(-c3ccc(Cl)c(Cl)c3)c(F)c2)CC1]

i.e., that form characterized by an XRPD pattern having characteristic peaks expressed in angle 2-theta at approximately those values shown in Table 1.

TABLE 1

| Degrees 2-theta |
|---|
| 17.02 |
| 19.29 |
| 20.44 |
| 23.67 |
| 25.58 |
| 30.03 |

When used with reference to XRPD peaks, the term "approximately" means that there is an uncertainty in the measurements of the degrees 2-theta (2θ) of ±0.2° (expressed in degrees 2-theta).

In another embodiment, the Form I crystalline polymorph is characterized by an XRPD pattern comprising characteristic peaks with approximate 2θ values as indicated in Table 2, and with relative intensities deviating by no more than ±30%, preferably no more than ±10% from the values given in Table 2.

TABLE 2

| Degrees 2-theta | Relative intensity (%) |
|---|---|
| 17.02 | 100.0 |
| 19.29 | 68.8 |
| 20.44 | 52.3 |
| 23.67 | 57.0 |
| 25.58 | 60.6 |
| 30.03 | 46.5 |

In another embodiment, the Form I crystalline polymorph is characterized by an XRPD pattern comprising characteristic peaks with approximate 2θ values as indicated in Table 3.

TABLE 3

| Diffraction Angle (°2θ) |
|---|
| 16.63 |
| 17.02 |
| 19.29 |
| 20.44 |
| 22.46 |
| 23.67 |
| 25.00 |
| 25.58 |
| 26.34 |
| 26.63 |
| 28.24 |
| 28.66 |
| 30.03 |
| 30.24 |
| 32.58 |

Figure 1:
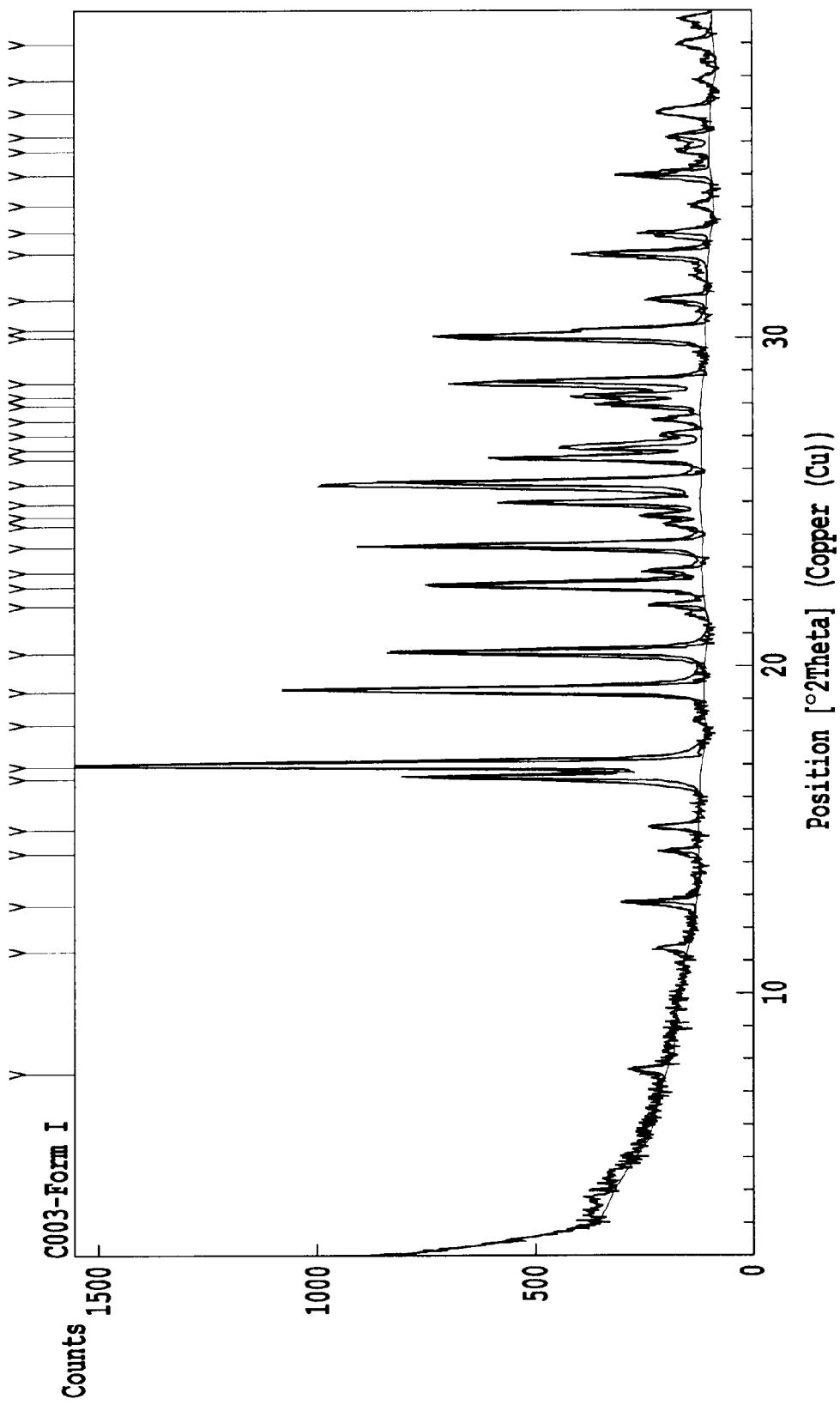
FIG. 1 shows the X-ray diffraction pattern (XRDP) of polymorph Form I of 1-(3',4'-dichloro-2-fluorobiphenyl-4-yl)cyclopropanecarboxylic acid.

The Form I polymorph can also be defined as having an XRPD pattern having characteristic peaks and relative intensities substantially as illustrated in FIG. 1.

Furthermore, the Form I crystalline polymorph can be characterized by its melting point. Therefore, the invention also encompasses a Form I crystalline polymorph of 1-(3',4'-dichloro-2-fluorobiphenyl-4-yl)cyclopropanecarboxylic acid having a melting temperature onset at about 200° C. and peaking at about 202° C. (as measured, for instance, by DSC).

In a second aspect, the invention relates to crystalline polymorph Form II of the compound of Formula I, namely that form characterized by an XRPD pattern having characteristic peaks expressed in angle 2-theta at approximately those values shown in Table 4.

TABLE 4

| Degrees 2-theta |
|---|
| 17.22 |
| 19.14 |
| 19.23 |
| 20.34 |
| 24.17 |
| 25.02 |

In another embodiment, the Form II crystalline polymorph is characterized by an XRPD pattern comprising characteristic peaks with approximate 2θ values as indicated in Table 5, and with relative intensities deviating by no more than ±30%, preferably no more than ±10% from the values given in Table 5.

TABLE 5

| Degrees 2-theta | Relative intensity (%) |
|---|---|
| 17.22 | 92.8 |
| 19.14 | 84.5 |
| 19.23 | 100.0 |
| 20.34 | 72.7 |
| 24.17 | 69.7 |
| 25.02 | 85.4 |

In another embodiment, the Form II crystalline polymorph is characterized by an XRPD pattern comprising characteristic peaks with approximate 2θ values as indicated in Table 6.

TABLE 6

| Diffraction Angle (°2θ) |
|---|
| 16.41 |
| 17.09 |
| 17.22 |
| 17.78 |
| 19.14 |
| 19.23 |
| 20.34 |
| 21.98 |
| 24.17 |
| 24.76 |
| 25.02 |
| 25.88 |
| 26.11 |
| 28.00 |
| 28.52 |
| 28.95 |
| 29.21 |
| 29.99 |
| 30.82 |

Figure 2:
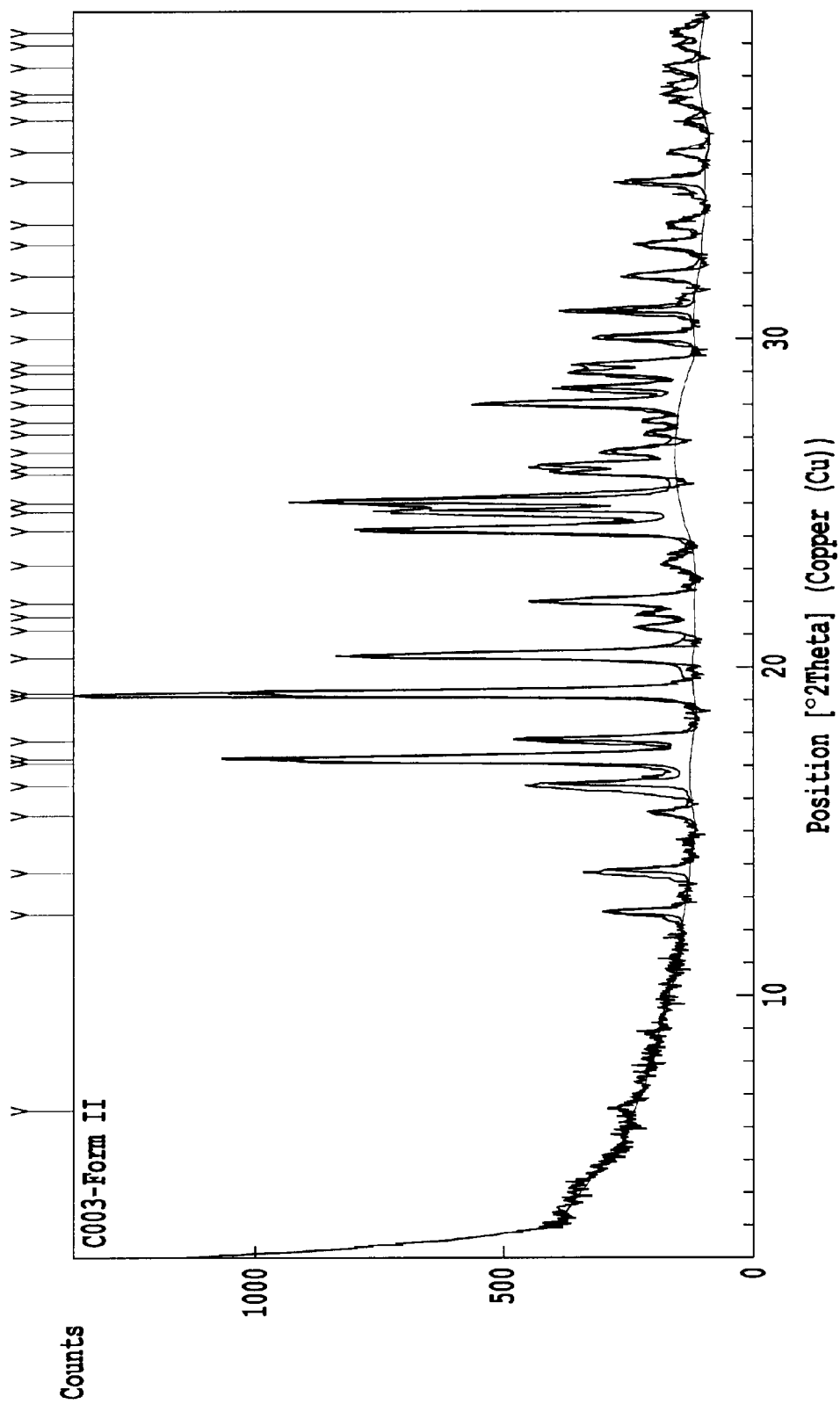
FIG. 2 shows the XRDP of polymorph Form II of 1-(3',4'-dichloro-2-fluorobiphenyl-4-yl)cyclopropanecarboxylic acid.

The Form II polymorph can also be defined as having an XRPD pattern having characteristic peaks and relative intensities substantially as illustrated in FIG. 2.

Furthermore, the Form II crystalline polymorph can be characterized by its melting point. Therefore, the invention also encompasses a crystalline polymorph of 1-(3',4'-dichloro-2-fluorobiphenyl-4-yl)cyclopropanecarboxylic acid having a melting temperature onset at about 200° C. and peaking at about 202° C.

In a third aspect the invention relates to Form III of the compound of Formula I, namely that form characterized by an XRPD pattern having characterized peaks expressed in angle 2-theta at approximately those values shown in Table 7.

TABLE 7

| Degrees 2-theta |
| --- |
| 19.37 |
| 19.46 |
| 20.45 |
| 20.64 |
| 23.97 |
| 24.16 |

Preferably the Form III crystalline polymorph is characterized by an XRPD pattern comprising characteristic peaks with approximate 2θ values as indicated in Table 8, and with relative intensities deviating by no more than ±30%, preferably no more than ±10% from the values given in Table 8.

TABLE 8

| Degrees 2-theta | Relative intensity (%) |
| --- | --- |
| 19.37 | 15.0 |
| 19.46 | 21.8 |
| 20.45 | 19.6 |
| 20.64 | 100.0 |
| 23.97 | 39.2 |
| 24.16 | 43.8 |

In another embodiment, the Form III crystalline polymorph is characterized by an XRPD pattern comprising characteristic peaks with approximate 2θ values as indicated in Table 9.

TABLE 9

| Diffraction Angle (°2θ) |
| --- |
| 19.37 |
| 19.46 |
| 20.45 |
| 20.64 |
| 23.97 |
| 24.16 |
| 29.50 |
| 29.97 |

Figure 3:
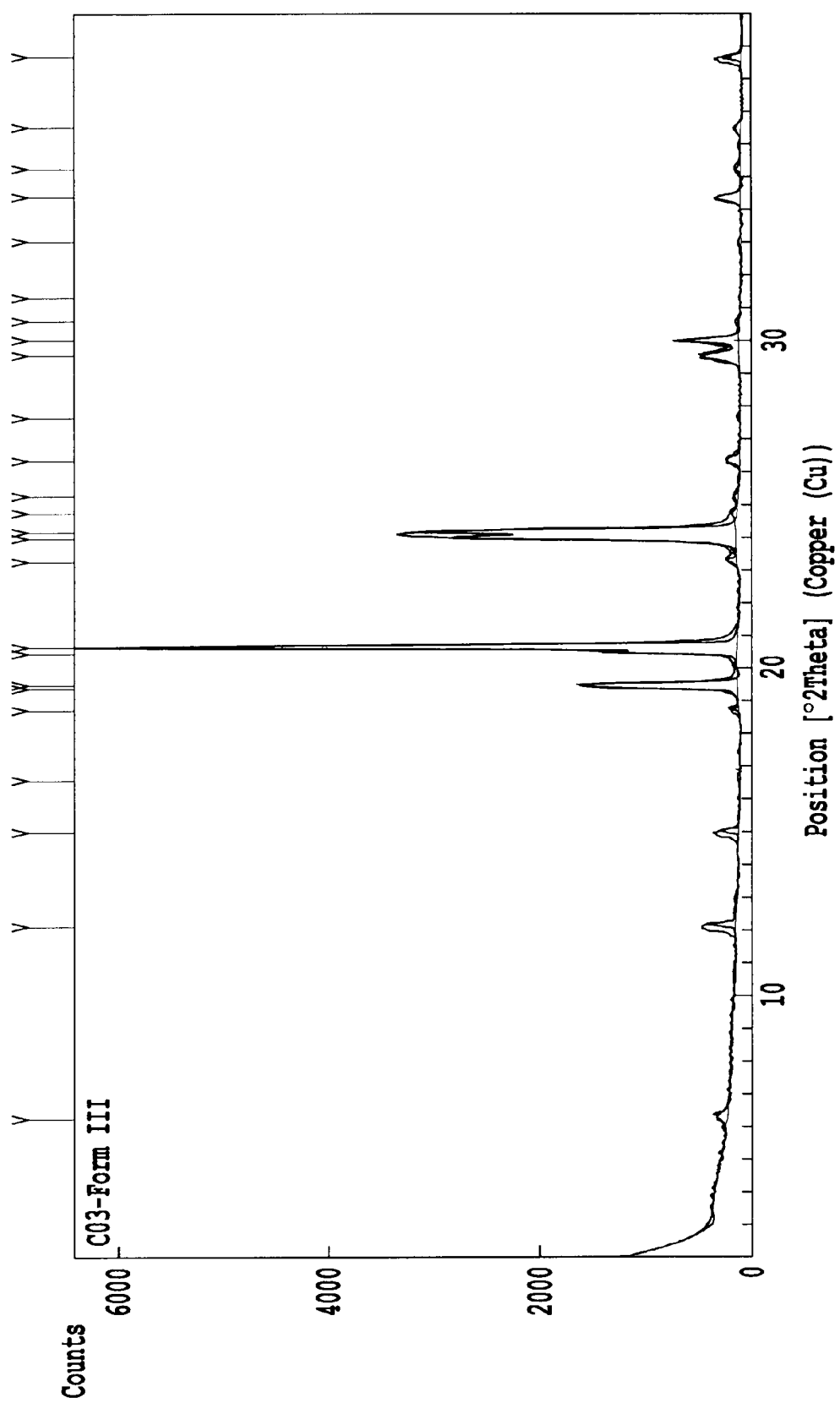
FIG. 3 shows the XRDP of polymorph Form III of 1-(3',4'-dichloro-2-fluorobiphenyl-4-yl)cyclopropanecarboxylic acid.

The Form III polymorph can also be defined as having an XRPD pattern having characteristic peaks and relative intensities substantially as illustrated in FIG. 3.

Furthermore, the Form III crystalline polymorph can be characterized by its melting point. Therefore, the invention also encompasses a crystalline polymorph of 1-(3',4'-dichloro-2-fluorobiphenyl-4-yl)cyclopropanecarboxylic acid having a melting temperature onset at about 198° C. and peaking at about 200° C.

The present invention encompasses polymorphs of 1-(3',4'-dichloro-2-fluorobiphenyl-4-yl)cyclopropanecarboxylic acid isolated in substantially pure form or when admixed with other substances, such as pharmaceutical excipients and/or therapeutic agents. A "substantially pure" isolated polymorph refers to a sample in which the polymorph is present in a substantial excess over other polymorphs of the same compound, i.e. in an amount exceeding 75%, more preferably exceeding 90%, even more preferably exceeding 95%, and most preferably exceeding 99% by weight of the total weight of the compound of Formula I in the sample.

The present invention also provides processes for preparing the polymorphs of the invention. Form I can be prepared under a variety of conditions, as shown in the Examples. In general terms, the compound of Formula I is dissolved in a suitable solvent, filtered, and then left to evaporate. Preferred solvents (depending on the recrystallization conditions) include 1,2-dimethoxy ethane, 1-butanol, 2-methoxy ethanol, acetone, acetonitrile, chloroform, dichloromethane, diethyl ether, dioxane, DMF, DMSO, ethanol, ethyl acetate, methanol, nitromethane, 1-propanol, and p-xylene. The recrystallization is preferably carried out at room temperature.

According to one method of preparing the polymorphic Form II of the compound of Formula I, the compound is first dissolved in dioxane, filtered, and then left to evaporate at room temperature.

According to one method of preparing the polymorphic Form III of the compound of Formula I, the compound is first dissolved in acetone, filtered, and then left to evaporate at room temperature.

As described in the Examples, attempts were made to prepare salts of the compound of Formula I using various different bases. Salts with Na, K, Ca, and with the basic amino acids L-Arginine, D-Arginine and L-Lysine were successfully prepared, but attempts to manufacture salts using the bases piperazine, morpholine, betaine, choline, imidazole, magnesium hydroxide and ammonia failed.

The Na, K, L-Arg and L-Lys salts of the present invention were tested and shown to have excellent solubility in water. Furthermore, these salts were found to have good stability when stored under conditions of high humidity. The preferred salts of the invention are the Arginine and Lysine salts of the compound of Formula I, because of the potentially harmful effects of administering the other salts in high dosages to patients having hypertension associated with Alzheimer's disease.

The present invention encompasses salts of 1-(3',4'-dichloro-2-fluorobiphenyl-4-yl)cyclopropanecarboxylic acid isolated in substantially pure form or when admixed with other substances, such as pharmaceutical excipients and/or therapeutic agents. A "substantially pure" isolated salt refers to a sample in which the salt is present in a substantial excess over other salts or free base of the same compound, i.e. in an amount exceeding 75%, more preferably exceeding 90%, even more preferably exceeding 95%, and most preferably exceeding 99% by weight of the total weight of the salts and free base of compound of Formula I in the sample.

Figure 4:
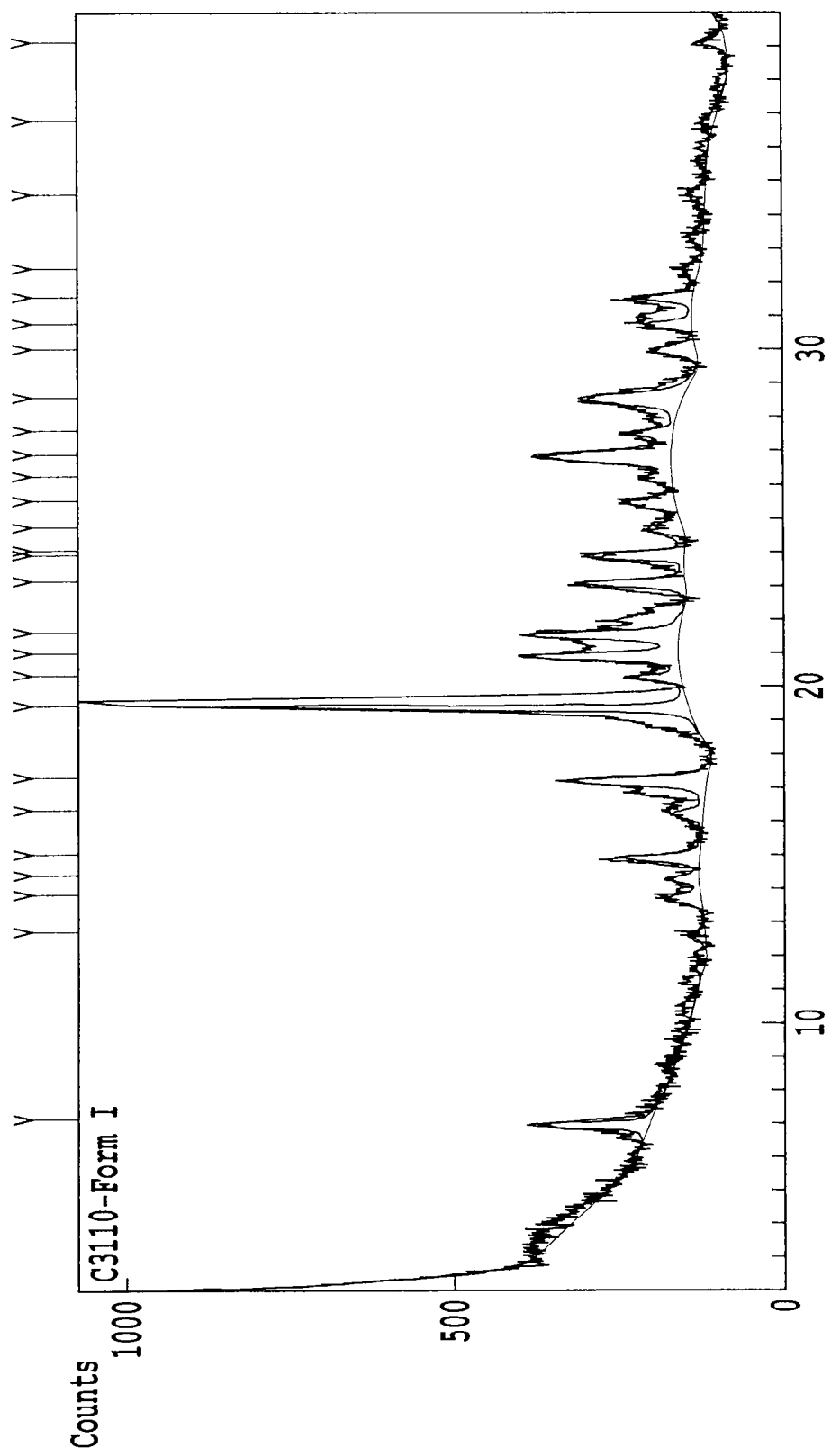
FIG. 4 shows the XRDP of the L-Lysine salt of 1-(3',4'-dichloro-2-fluorobiphenyl-4-yl)cyclopropanecarboxylic acid.

The L-Lysine salt of the compound of Formula I has been recrystallized and has been shown to adopt a Form I structure (FIG. 4). Thus, the invention also relates to polymorphic Form I of the L-Lysine salt, and a method for manufacturing the L-Lysine Form I polymorph comprising dissolving the salt in ethanol, methanol or water, filtering the resulting solution, and allowing the solution to evaporate at room temperature.

The present invention also provides pharmaceutical compositions comprising a polymorph or salt according to the invention, and one or more pharmaceutically acceptable carriers or excipients, such as carriers, diluents, wetting agents, emulsifying agents, binders, coatings, fillers, glidants, lubricants, disintegrants, preservatives, stabilizers, surfactants, pH buffering substances, flavouring agents and the like. Comprehensive guidance on pharmaceutical excipients is given in *Remington's Pharmaceutical Sciences Handbook*, XVII Ed. Mack Pub., N.Y., U.S.A., which is incorporated herein by reference in its entirety.

In one embodiment, pharmaceutical compositions of the present invention comprise a crystalline polymorph or salt of the compound of Formula I in combination with one or more other therapeutically active substances, in particular any pharmaceutical substance used for prevention or treatment of Alzheimer's Disease.

The pharmaceutical compositions of the present invention may be formulated for administration by any convenient route, e.g. by oral, parenteral, topical, inhalation, buccal, nasal, rectal, vaginal, transdermal administration. Suitable dosage forms can include tablets, capsules, lozenges, suppositories, solutions, emulsions, suspensions, syrups, ointments, creams, oils, and powders. Preferably, the pharmaceutical compositions of the invention will be administered orally using appropriate dosage forms, such as capsules or tablets.

The dosage of the compounds of Formula I and their salts can vary within wide limits depending on the nature of the disease to be treated, the type of patient, and the mode of administration. A person skilled in the art can determine a therapeutically effective amount for each patient and thereby define the appropriate dosage. A typical daily dosage might fall within the range of 400 mg to 800 mg, administered in a single or multiple daily dosage units. Thus, a single dose of the pharmaceutical preparations of the invention conveniently comprises between about 100 and 800 mg of a polymorph or salt of the compound of Formula I.

The polymorphs and salts of the present invention may be of use in the treatment or prophylaxis of any disease or condition where it is advantageous to modulate gamma secretase activity. In particular, these substances may be useful in preventing or treating Alzheimer's disease.

Other embodiments of the invention include:

Polymorph Form I having characteristic XRPD peaks of relative intensities of approximately:

| Degrees 2-theta | Relative intensity (%) |
|---|---|
| 17.02 | 100.0 |
| 19.29 | 68.8 |
| 20.44 | 52.3 |
| 23.67 | 57.0 |
| 25.58 | 60.6 |
| 30.03 | 46.5 |

Polymorph Form I characterized in that it has a melting temperature onset at about 200° C., and peaking at about 202° C.

Polymorph Form II, having characteristic XRPD peaks of relative intensities of approximately:

| Degrees 2-theta | Relative intensity (%) |
|---|---|
| 17.22 | 92.8 |
| 19.14 | 84.5 |
| 19.23 | 100.0 |
| 20.34 | 72.7 |
| 24.17 | 69.7 |
| 25.02 | 85.4 |

Polymorph Form II characterized in that it has a melting temperature onset at about 200° C., and peaking at about 202° C.

Polymorph Form III having characteristic XRPD peaks of relative intensities of approximately:

| Degrees 2-theta | Relative intensity (%) |
|---|---|
| 19.37 | 15.0 |
| 19.46 | 21.8 |
| 20.45 | 19.6 |
| 20.64 | 100.0 |
| 23.97 | 39.2 |
| 24.16 | 43.8 |

Polymorph Form III characterized in that it has a melting temperature onset at about 198° C., and peaking at about 200° C.

The compound 1-(3',4'-dichloro-2-fluorobiphenyl-4-yl)cyclopropanecarboxylic acid, at least 70% of which is present as crystalline polymorph Form I.

The compound 1-(3',4'-dichloro-2-fluorobiphenyl-4-yl)cyclopropanecarboxylic acid, at least 70% of which is present as crystalline polymorph Form II.

The compound 1-(3',4'-dichloro-2-fluorobiphenyl-4-yl)cyclopropanecarboxylic acid, at least 70% of which is present as crystalline polymorph Form III.

Any of the polymorphs of the invention for use as a medicament.

A crystalline polymorph according to the invention for use in the prevention or treatment of Alzheimer's Disease.

A method of preventing or treating an amyloidogenic disease, such as Alzheimer's Disease, comprising administering to a patient in need of such treatment a therapeutically effective amount of a crystalline polymorph of the invention.

A method of preparing crystalline Form I of 1-(3',4'-dichloro-2-fluorobiphenyl-4-yl)cyclopropanecarboxylic acid, comprising dissolving the compound in an excess of solvent, filtering the resulting solution, and allowing the solution to crystallize at room temperature, wherein the solvent is selected from the group consisting of: acetonitrile, chloroform, dichloromethane, diethyl ether, ethanol, ethyl acetate, methanol, and nitromethane.

A method of preparing crystalline Form II of 1-(3',4'-dichloro-2-fluorobiphenyl-4-yl)cyclopropanecarboxylic acid, comprising dissolving the compound in an excess of dioxane, filtering the resulting solution, and allowing the solution to crystallize at room temperature.

A method of preparing crystalline Form III of 1-(3',4'-dichloro-2-fluorobiphenyl-4-yl)cyclopropanecarboxylic acid, comprising dissolving the compound in an excess of acetone, filtering the resulting solution, and allowing the solution to crystallize at room temperature.

An L-Lysine, L-Arginine or D-Arginine salt of 1-(3',4'-dichloro-2-fluorobiphenyl-4-yl)cyclopropanecarboxylic acid.

A method of preparing crystalline Form I of the L-Lysine salt of 1-(3',4'-dichloro-2-fluorobiphenyl-4-yl)cyclopropanecarboxylic acid, comprising dissolving the salt in ethanol, methanol, or water; filtering the resulting solution; and allowing the solution to evaporate at room temperature.

Crystalline Form I L-Lysine salt of 1-(3',4'-dichloro-2-fluorobiphenyl-4-yl)cyclopropanecarboxylic acid characterized in that it provides an X-ray diffraction XRPD) pattern substantially in accordance with FIG. 4.

A salt according to the invention for use as a medicament.

A salt according to the invention for use in the prevention or treatment of Alzheimer's Disease.

A method of preventing or treating an amyloidogenic disease, such as Alzheimer's Disease, comprising administering to a patient in need of such treatment a therapeutically effective amount of a salt of the invention.

Other features of the invention will become apparent in the course of the following descriptions of exemplary embodiments which are given for illustration of the invention and are not intended to be limiting thereof.

EXAMPLES

Example 1

Identification of Novel Polymorphs:
Recrystallization Experiments 1.1. Room Temperature Recrystallization.

0.05 g of 1-(3',4'-dichloro-2-fluorobiphenyl-4-yl)cyclopropanecarboxylic acid was dissolved in 4 mL of solvent with stirring. After about 1 hour of stirring the solution obtained was filtered through a Whatman filter (0.45 μm) and left to evaporate at room temperature for either 3 days or 1 week. Table 10 shows the outcome of the recrystallization using different solvents. Polymorphic forms I, II and III were identified and characterized by XRPD and DSC.

XRPD analyses were performed using an X'Pert Pro instrument with a Cu anode and equipped with an X'Celerator (PANalytical, Netherlands) in continuous scanning mode at 25° C., with a scan step size (°2θ) of 0.017 and a scan step time of 12.9 seconds. The characteristic XRPD spectra of Forms I, II and III are illustrated in FIGS. 1-3, respectively.

DSC analyses were carried out using a DCS Diamond instrument (Perkin Elmer). Scan settings were 5° C./minute (PAN: open). Form I and Form II crystals were found to have a $T_{onset}$ at about 200° C., the melting temperature peaking at about 202° C. Form III crystals had a $T_{onset}$ of about 198° C., the melting temperature peaking at about 200° C.

TABLE 10

| Solvent | Result of RT crystallization attempt |
| --- | --- |
| 1,2-dimethoxy ethane | Yield too low to characterize |
| 1-butanol | Yield too low to characterize |
| 2-methoxy ethanol | Yield too low to characterize |
| acetone | Form III |
| acetonitrile | Form I |
| c-hexane | Yield too low to characterize |
| chloroform | Form I |
| dichloromethane | Form I |
| diethyl ether | Form I |
| dioxane | Form II |
| DMF | Yield too low to characterize |
| DMSO | Yield too low to characterize |
| ethanol | Form I |
| ethyl acetate | Form I |
| hexane | Negative (low solubility) |
| 1-propanol | Yield too low to characterize |
| iso-propyl ether | Yield too low to characterize |
| methanol | Form I |
| methyl ethyl ketone | Yield too low to characterize |
| nitromethane | Form I |
| p-xylene | Negative (low solubility) |
| t-butyl methyl ether | Yield too low to characterize |
| tert-butanol | Yield too low to characterize |
| THF | Yield too low to characterize |
| water | Negative (low solubility) |

1.2. Low Temperature Recrystallization.

0.05 g of 1-(3',4'-dichloro-2-fluorobiphenyl-4-yl)cyclopropane-carboxylic acid was dissolved in 4 mL of solvent with stirring. After about 1 hour of stirring the solution obtained was filtered through a Whatman filter (0.45 μm) and left to evaporate at 5° C. for 1-2 weeks. Table 11 shows the outcome of the recrystallization using different solvents. Polymorphic forms I and II were identified and characterized by XRPD and DSC as described above.

TABLE 11

| Solvent | Result of low temperature crystallization attempt |
| --- | --- |
| 1,2-dimethoxy ethane | Yield too low to characterize |
| 1-butanol | Yield too low to characterize |
| 2-methoxy ethanol | Yield too low to characterize |
| acetone | Form I |
| acetonitrile | Form I |
| c-hexane | Yield too low to characterize |
| chloroform | Form I |
| dichloromethane | Form I |
| diethyl ether | Form I |
| dioxane | Form I + Form II |
| DMF | Yield too low to characterize |
| DMSO | Yield too low to characterize |
| ethanol | Form I |
| ethyl acetate | Form I |
| hexane | Negative (low solubility) |
| 1-propanol | Yield too low to characterize |
| iso-propyl ether | Yield too low to characterize |
| methanol | Form I |
| methyl ethyl ketone | Yield too low to characterize |
| nitromethane | Form I |
| p-xylene | Negative (low solubility) |
| t-butyl methyl ether | Yield too low to characterize |
| tert-butanol | Yield too low to characterize |
| THF | Yield too low to characterize |
| water | Negative (low solubility) |

1.3. High Temperature Recrystallization.

0.05 g of 1-(3',4'-dichloro-2-fluorobiphenyl-4-yl)cyclopropanecarboxylic acid was dissolved in 4 mL of solvent with stirring. After about 1 hour of stirring the solution obtained was filtered through a Whatman filter (0.45 μm) and left to evaporate at 60° C. for 2-3 weeks. Table 12 shows the outcome of the recrystallization using different solvents. Polymorphic form I was identified and characterized by XRPD and DSC as described above.

TABLE 12

| Solvent | Result of high temperature crystallization attempt |
| --- | --- |
| 1,2-dimethoxy ethane | Form I |
| 1-butanol | Form I |
| 2-methoxy ethanol | Form I |
| acetone | Yield too low to characterize |
| acetonitrile | Form I |
| c-hexane | Yield too low to characterize |
| chloroform | Yield too low to characterize |
| dichloromethane | Yield too low to characterize |
| diethyl ether | Yield too low to characterize |
| dioxane | Form I |
| DMF | Form I |
| DMSO | Form I |
| ethanol | Yield too low to characterize |
| ethyl acetate | Yield too low to characterize |
| hexane | Negative (low solubility) |
| 1-propanol | Form I |
| iso-propyl ether | Yield too low to characterize |
| methanol | Yield too low to characterize |
| methyl ethyl ketone | Yield too low to characterize |
| nitromethane | Form I |
| p-xylene | Form I |
| t-butyl methyl ether | Yield too low to characterize |

TABLE 12-continued

| Solvent | Result of high temperature crystallization attempt |
|---|---|
| tert-butanol | Yield too low to characterize |
| THF | Yield too low to characterize |
| water | Negative (low solubility) |

1.4. Preparation of Slurries.

The suspensions were prepared by dissolving 0.05 g of 1-(3',4'-dichloro-2-fluorobiphenyl-4-yl)cyclopropanecarboxylic acid solid in 2 mL of solvent. The suspensions were stirred for 1 month at room temperature, filtered through Whatman 0.45 µm filters and measured before the sample began to dry. The results are shown in Table 13. Polymorphic forms I and II were identified and characterised by XRPD and DSC as described above. In all cases where the compound was not completely soluble in the solvent, slurries yielded only Form I.

EXAMPLES TABLE 13

| Solvent | Result |
|---|---|
| methanol | Form I |
| acetone | Form I |
| acetonitrile | Form I |
| THF | Form I |
| isopropyl ether | Form I |
| toluene | Form I |
| ethyl acetate | Form I |
| 1-propanol | Form I |
| dioxane | Form II |
| p-xylene | Form I |
| methyl ethyl ketone | Form I |
| 1-butanol | Form I |
| chloroform | Form I |
| dichloromethane | Form I |
| hexane | Form I |
| ethanol | Form I |
| nitromethane | Form I |
| water | Form I |
| TBME | Form I |
| c-hexane | Form I |
| diethyl ether | Form I |

The experiment was repeated, this time stirring the slurries for 7 days at room temperature instead of 30 days. The crystallization results were the same.

Example 2

Preparation and Characterization of Salts of 1-(3',4'-dichloro-2-fluorobiphenyl-4-yl)cyclopropanecarboxylic acid 2.1. Salt Screening.

$1.5 \times 10^{-4}$ mol of 1-(3',4'-dichloro-2-fluorobiphenyl-4-yl)cyclopropanecarboxylic acid (0.500 g) and $1.5 \times 10^{-4}$ mol of base (summarized in Examples Table 5) were added to 5 ml water, and stirred at 500 rpm and 40° C. for 1 hour while monitoring the pH values. When the pH value was about 7, the solution was filtered and concentrated under vacuum. A pink powder was obtained for each salt. The results are shown in Table 14.

TABLE 14

| Base | Quantity | Result |
|---|---|---|
| Sodium hydroxide | 0.06 g | Salt obtained |
| Potassium hydroxide | 0.084 g | Salt obtained |

TABLE 14-continued

| Base | Quantity | Result |
|---|---|---|
| Calcium hydroxide | 0.111 g | Salt obtained |
| L-Arginine | 0.261 g | Salt obtained |
| L-Lysine | 0.219 g | No salt |
| D-Arginine | 0.261 g | Salt obtained |
| Piperazine | 0.129 g | No salt |
| Morpholine | 0.130 g (d = 1, mL = 0.130) | No salt |
| Betaine | 0.175 g | No salt |
| Choline | 0.181 g (d = 1.09; mL = 0.166) | No salt |
| Imidazole | 0.102 g | No salt |
| Magnesium hydroxide | 0.087 g | No salt |
| Ammonia | 0.170 mL | No salt |

The experiment was then repeated with ethanol instead of water, using those bases that failed to yield a salt in the first experiment. The results are shown in Table 15.

TABLE 15

| Base | Quantity | Result |
|---|---|---|
| L-Lysine | 0.219 g | Salt obtained |
| Choline | 0.181 g (d = 1.09; mL = 0.166) | No salt |
| Imidazole | 0.102 g | No salt |
| Magnesium hydroxide | 0.087 g | No salt |
| Ammonia | 0.170 mL | No salt |

Each of the salts obtained was characterized by X-ray powder diffraction (XRPD), Thermogravimetric analysis (TGA), and Differential Scanning calorimetry (DSC). Furthermore, the stabilities of the sodium, potassium, L-Arginine and L-Lysine salts were tested by storage for 7 days at room temperature and 80% relative humidity. No changes were seen in the XRPD pattern.

2.2. Thermodynamic Solubility of Salts.

Each of the sodium, potassium, L-Arg and L-Lys salts prepared as described above was dissolved in water at a temperature of 37° C., pH 6.8-7.4 at a stirring rate of 500 rpm for 24 hours. The results are shown in Table 16.

TABLE 16

| Salt | Amount | Volume of water | Solubility g/L |
|---|---|---|---|
| Sodium | 81.5 mg | 4 mL | 20.4 |
| Potassium | 12.6 mg | 2 mL | 6.3 |
| L-Arginine | 60.6 mg | 4 mL | 15.2 |
| L-Lysine | 146.4 mg | 4 mL | 36.6 |

These solubility values are predictive of good in vivo solubility.

2.3. Re-Crystallization of L-Lysine Salt.

The L-Lysine salt was dissolved in 4 mL of solvent with stirring. After about 1 hour of stirring the solution obtained was filtered through a Whatman filter (0.45 µm) and left to evaporate at room temperature for 3 days or 1 week. Table 17 shows the outcome of the recrystallization. The crystals were analysed by XRPD as described above. The recrystallization of the L-Lysine salt in chloroform produced a sample having an identical diffraction pattern to that of the free base.

TABLE 17

| Solvent | Result of room temperature crystallization attempt |
|---|---|
| 1,2-dimethoxy ethane | Yield too low to characterize |
| 1-butanol | Yield too low to characterize |
| 2-methoxy ethanol | Yield too low to characterize |

TABLE 17-continued

| Solvent | Result of room temperature crystallization attempt |
|---|---|
| acetone | Yield too low to characterize |
| acetonitrile | Yield too low to characterize |
| c-hexane | Yield too low to characterize |
| chloroform = | free base |
| dichloromethane | Yield too low to characterize |
| diethyl ether | Yield too low to characterize |
| dioxane | Yield too low to characterize |
| DMF | Yield too low to characterize |
| DMSO | Yield too low to characterize |
| ethanol | Form I |
| ethyl acetate | Yield too low to characterize |
| hexane | Yield too low to characterize |
| 1-propanol | Yield too low to characterize |
| iso-propyl ether | Yield too low to characterize |
| methanol | Form I |
| methyl ethyl ketone | Yield too low to characterize |
| nitromethane | Yield too low to characterize |
| p-xylene | Yield too low to characterize |
| t-butyl methyl ether | Yield too low to characterize |
| tert-butanol | Yield too low to characterize |
| THF | Yield too low to characterize |
| water | Form I |

An XRPD diagram of the L-Lysine form I salt is provided in FIG. 4. The Form I salt is characterized by an XRPD pattern comprising characteristic peaks with approximate 2θ values as indicated in the Table 18, and with relative intensities deviating by no more than ±30%, preferably no more than ±10% from the values given in Table 18.

TABLE 18

| Degrees 2-theta | Relative intensity (%) |
|---|---|
| 7.09 | 21.7 |
| 17.25 | 28.1 |
| 19.40 | 100.0 |
| 20.95 | 29.6 |
| 21.58 | 29.8 |
| 26.85 | 25.3 |

When the experiment was repeated at recrystallization temperature of 5° C. for 1-2 weeks similar crystallization results were achieved.

When the experiment was repeated at a recrystallization temperature of 60° C. for 2-3 days the only solvent yielding crystals was water (Form I crystals).

Slurries were prepared by dissolving 0.050 g of the L-Lysine salt in 2 mL of solvent. The suspensions were stirred for 7 days at room temperature, filtered through Whatman filters and measured before the sample began to dry. The crystals were analysed by XRPD as described above. The results are shown in Table 19 (C03=identical to free base):

TABLE 19

| Solvent | Result |
|---|---|
| methanol | Form I |
| acetone | Form I |
| acetonitrile | Form I |
| ethyl acetate | Form I |
| 1-propanol | Form I |
| dioxane | Form I |
| p-xylene | Form I |
| 1-butanol | Form I |
| chloroform | Form I + C03 |
| dichloromethane | Form I |
| hexane | Form I |
| ethanol | Form I |
| nitromethane | Form I |

TABLE 19-continued

| Solvent | Result |
|---|---|
| water | — |
| 1,2-dimethoxy ethane | Form I |
| c-hexane | Form I |
| diethyl ether | Form I |
| 2-methoxy ethanol | Form I |
| DMF | Form I + amorphous |
| DMSO | amorphous |

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. Crystalline 1-(3',4'-dichloro-2-fluorobiphenyl-4-yl)cyclopropanecarboxylic acid, which is selected from the group consisting of:
   crystalline 1-(3',4'-dichloro-2-fluorobiphenyl-4-yl)cyclopropanecarboxylic acid, which has an X-ray powder diffraction pattern which has diffraction peaks expressed in angle 2-theta, ±0.2°, at 17.22°, 19.14°, 19.23°, 20.34°, 24.17°, and 25.02°; and
   crystalline 1-(3',4'-dichloro-2-fluorobiphenyl-4-yl)cyclopropanecarboxylic acid, which has an X-ray powder diffraction pattern which has diffraction peaks expressed in angle 2-theta, ±0.2°, at 19.37°, 19.46°, 20.45°, 20.64°, 23.97°, and 24.16°.

2. Crystalline 1-(3',4'-dichloro-2-fluorobiphenyl-4-yl)cyclopropanecarboxylic acid, which has an X-ray powder diffraction pattern which has diffraction peaks expressed in angle 2-theta, ±0.2°, at 17.22°, 19.14°, 19.23°, 20.34°, 24.17°, and 25.02°.

3. Crystalline 1-(3',4'-dichloro-2-fluorobiphenyl-4-yl)cyclopropanecarboxylic acid according to claim 2, which has an X-ray diffraction (XRPD) pattern substantially in accordance with FIG. 2.

4. Crystalline 1-(3',4'-dichloro-2-fluorobiphenyl-4-yl)cyclopropanecarboxylic acid, which has an X-ray powder diffraction pattern which has diffraction peaks expressed in angle 2-theta, ±0.2°, at 19.37°, 19.46°, 20.45°, 20.64°, 23.97°, and 24.16°.

5. Crystalline 1-(3',4'-dichloro-2-fluorobiphenyl-4-yl)cyclopropanecarboxylic acid according to claim 4, which has an X-ray diffraction (XRPD) pattern substantially in accordance with FIG. 3.

6. A pharmaceutical composition, comprising substantially pure crystalline 1-(3',4'-dichloro-2-fluorobiphenyl-4-yl)cyclopropanecarboxylic acid according to claim 1 and a pharmaceutically acceptable carrier.

7. A method for the treatment of Alzheimer's Disease, comprising administering to a subject in need thereof an effective amount of crystalline 1-(3',4'-dichloro-2-fluorobiphenyl-4-yl)cyclopropanecarboxylic acid according to claim 1.

8. Crystalline 1-(3',4'-dichloro-2-fluorobiphenyl-4-yl)cyclopropanecarboxylic acid according to claim 2, which has an X-ray powder diffraction pattern which has diffraction peaks expressed in angle 2-theta, ±0.2°, at 16.41°, 17.09°, 17.22°, 17.78°, 19.14°, 19.23°, 20.34°, 21.98°, 24.17°, 24.76°, 25.02°, 25.88°, 26.11°, 28.00°, 28.52°, 28.95°, 29.21°, 29.99°, and 30.82°.

9. Crystalline 1-(3',4'-dichloro-2-fluorobiphenyl-4-yl)cyclopropanecarboxylic acid according to claim 4, which has an X-ray powder diffraction pattern which has diffraction peaks expressed in angle 2-theta, ±0.2°, at 19.37°, 19.46°, 20.45°, 20.64°, 23.97°, 24.16°, 29.50°, and 29.97°.

10. A pharmaceutical composition, comprising substantially pure crystalline 1-(3',4'-dichloro-2-fluorobiphenyl-4-yl)cyclopropanecarboxylic acid according to claim 2 and a pharmaceutically acceptable carrier.

11. A pharmaceutical composition, comprising substantially pure crystalline 1-(3',4'-dichloro-2-fluorobiphenyl-4-yl)cyclopropanecarboxylic acid according to claim 8 and a pharmaceutically acceptable carrier.

12. A pharmaceutical composition, comprising substantially pure crystalline 1-(3',4'-dichloro-2-fluorobiphenyl-4-yl)cyclopropanecarboxylic acid according to claim 4 and a pharmaceutically acceptable carrier.

13. A pharmaceutical composition, comprising substantially pure crystalline 1-(3',4'-dichloro-2-fluorobiphenyl-4-yl)cyclopropanecarboxylic acid according to claim 9 and a pharmaceutically acceptable carrier.

14. A method for the treatment of Alzheimer's Disease, comprising administering to a subject in need thereof an effective amount of crystalline 1-(3',4'-dichloro-2-fluorobiphenyl-4-yl)cyclopropanecarboxylic acid according to claim 2.

15. A method for the treatment of Alzheimer's Disease, comprising administering to a subject in need thereof an effective amount of crystalline 1-(3',4'-dichloro-2-fluorobiphenyl-4-yl)cyclopropanecarboxylic acid according to claim 8.

16. A method for the treatment of Alzheimer's Disease, comprising administering to a subject in need thereof an effective amount of crystalline 1-(3',4'-dichloro-2-fluorobiphenyl-4-yl)cyclopropanecarboxylic acid according to claim 4.

17. A method for the treatment of Alzheimer's Disease, comprising administering to a subject in need thereof an effective amount of crystalline 1-(3',4'-dichloro-2-fluorobiphenyl-4-yl)cyclopropanecarboxylic acid according to claim 9.

* * * * *